United States Patent [19]

Spann

[11] 4,135,504

[45] Jan. 23, 1979

[54] ORTHOPEDIC SUPPORT

[76] Inventor: Donald C. Spann, 5 Ferncreek Ct., Greenville, S.C. 29607

[21] Appl. No.: 780,761

[22] Filed: Mar. 24, 1977

[51] Int. Cl.² ............................................. A61F 3/00
[52] U.S. Cl. .................................... 128/80 A; 128/149
[58] Field of Search ................ 128/80 R, 80 A, 134, 128/68, 68.1, 149, 133, DIG. 15

[56] References Cited

U.S. PATENT DOCUMENTS

| | | | |
|---|---|---|---|
| 3,228,399 | 1/1966 | Riedell | 128/361 |
| 3,423,773 | 1/1969 | Yamate | 128/80 R |
| 3,505,994 | 4/1970 | Smith | 128/80 R |
| 3,901,228 | 8/1975 | Brown | 128/133 |
| 4,000,736 | 1/1977 | Bruscemi | 128/80 R |

*Primary Examiner*—Lawrence W. Trapp
*Attorney, Agent, or Firm*—Bailey, Dority & Flint

[57] ABSTRACT

An abduction pillow is illustrated wherein a wedge-shaped body is constructed of synthetic foam material for positioning the limbs in cushioned fixed divergent position and means are also illustrated for supporting and cradling the foot and ankle portions of an orthopedic patient.

6 Claims, 5 Drawing Figures

ORTHOPEDIC SUPPORT

BACKGROUND OF THE INVENTION

Abduction pillows heretofore utilized were relatively rigid and covered with an air impervious plastic material. Such abduction pillows offered rigidity and failed to sufficiently depress or flex at the pressure points exerted thereon by the limbs. Since the surface of former abduction pillows is relatively smooth, the limbs tended to move or slide thereon rather than remain completely immobilized.

Accordingly, it is an important object of this invention to provide an abduction pillow constructed of foam material which will depress relatively easily to minimize discomfort and injury to the user at the pressure points exerted by the limbs. Any covering as formerly utilized causing a hummock effect with failure to cradle or conform to the configuration of the limb is avoided.

Another important object of the present invention is to provide an uncovered foam abduction pillow which makes it possible to utilize the friction of the material in combination with the conformable features of the material to completely immobilize the limb so as to eliminate internal and external rotation thereof.

Another important object of the invention is to provide an abduction pillow of synthetic foam material which utilizes soft straps which are also constructed of foam material with convenient fastening means so as to avoid the use of straps constructed of textile material. During the use of abduction pillows a prolonged period of immobiliation is often necessary and loss of circulation resulting from the strapping heretofore utilized is avoided.

BRIEF DESCRIPTION OF THE INVENTION

It has been found that abduction pillows may be provided for immobilizing the lower limbs of orthopedic patients by utilizing a flat wedge-shaped body of synthetic foam material of uniform substantially rectangular cross-section and utilizing elongated strips of foam as strapping for the positioning of the limbs against the diverging sides of the wedge-shaped body and providing a block at the lower corners thereof for supporting the foot and ankle portions of the limbs. The block portions are also constructed of synthetic foam material and have an elongated internal cavity in a longitudinal portion thereof for receiving the foot and ankle and are provided with a slotted opening for the reception thereof. These cradle blocks may be utilized on occasion without the wedge-shaped body providing an independent support means. A remote portion of the block provides a support for the foot preventing foot drop during prolonged use of the abduction pillow. A plurality of longitudinal slots are provided adjacent an entrance to the elongated opening within the block and adjacent the foot portion for providing deformability of isolated portions of the block so as to provide more pronounced yieldability in these areas to support the limb with a minimum of pressure thereagainst.

The uncovered foam material serves a two-fold purpose the first being to provide a uniform dispersion of pressure. Any covering, especially plastic will not let the pillow depress to avoid pressure points. Any covering will cause a hummock effect. In the abduction pillows that are covered there is little or no cradling of the leg. The uncovered foam of the present pillow effectively utilizes the friction, which makes the foam unmovable on skin or cloth. This friction element also keeps the legs immobilized. Therefore, internal and external rotation of the limbs is avoided. Because the straps are made entirely of foam they are unlike any of the other abduction pillow straps which are usually made of nylon straps that can cut into the legs, cut off circulation and irritate the skin. There is also a possibility of nerve damage with such non-elastic straps and the possibility of such damage is minimized. Since the pillow offers full support from the pubic area all the way to the ankle, total support facilitating turning of the patient is provided. The pillow can be custom cut for each patient. Areas can be readily cut away to relieve unusual pressure areas.

BRIEF DESCRIPTION OF THE DRAWINGS

The construction designed to carry out the invention will be hereinafter described, together with other features thereof.

The invention will be more readily understood from a reading of the following specification and by reference to the accompanying drawings forming a part therof, wherein an example of the invention is shown and wherein.

DESCRIPTION OF A PREFERRED EMBODIMENT

The drawings illustrate an abduction pillow for immobilizing the lower limbs of orthopedic patients including a flat wedge shaped body A constructed of uncovered synthetic foam material tapering outwardly at opposite sides. The wedge shaped body is of uniform thickness and of substantially rectangular cross-section. Spaced strapping B is constructed of flat substantially rectangular strips of synthetic foam material extending about spaced portions of each limb fixing same against respective sides of the body maintaining the limbs in divergent fixed positions corresponding to the divergent disposition of the sides. A block C is constructed of synthetic foam material and has an internal cavity therein carried adjacent a lower corner of said wedge shaped body for receiving and supporting the foot and ankle portions of the limbs.

Figure 1:
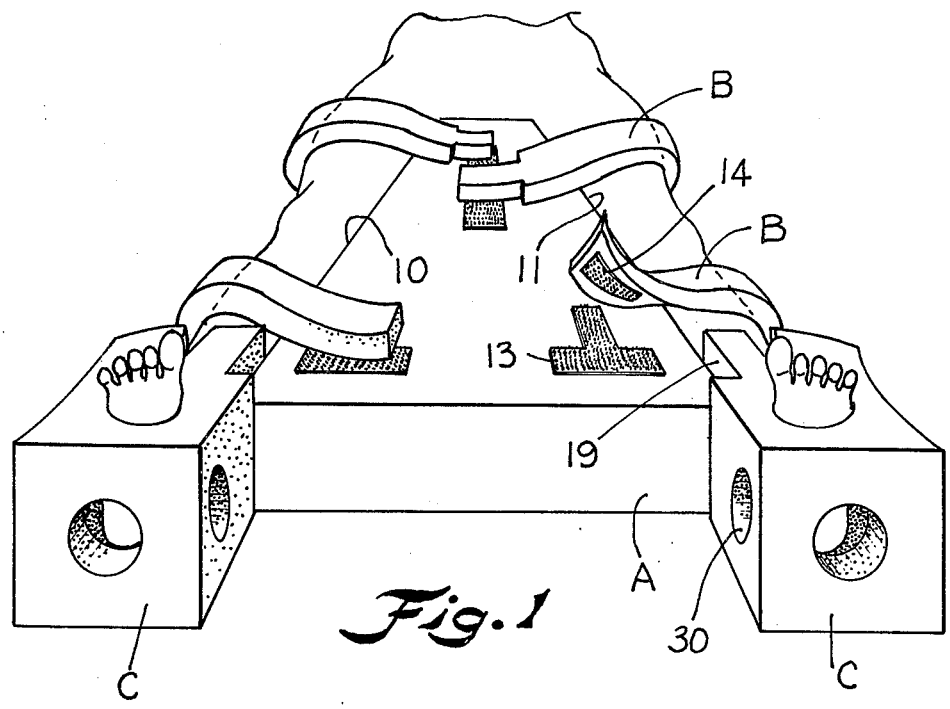
FIG. 1 is a perspective view illustrating an abduction pillow constructed in accordance with the present invention positioning the limbs of an orthopedic patient.
Figure 4:
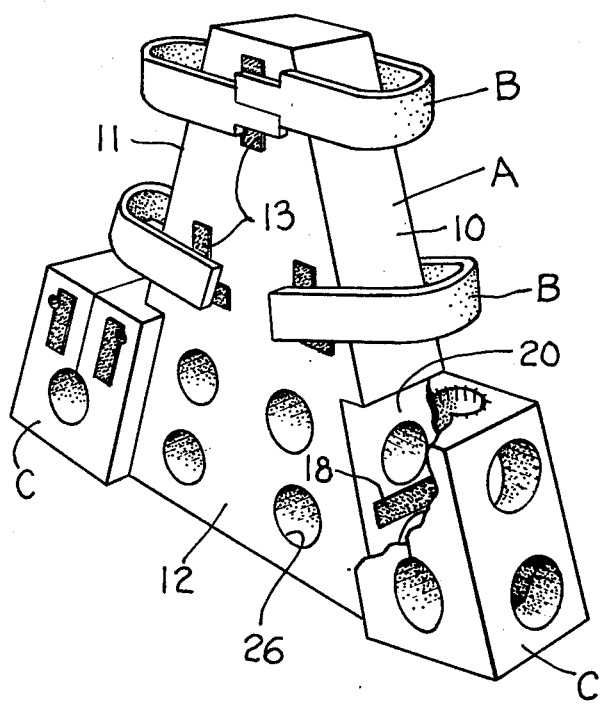
FIG. 4 is a perspective view further illustrating the abduction pillow in slightly modified form.

Referring more particularly to FIGS. 1 and 4, it will be noted that the wedge shaped body A has a pair of diverging sides 10 and 11 for maintaining the limbs in diverging position as is desirable, for example, following surgery for replacing the hip joints. Since the foam block forming the wedge shaped body is uncovered, the sides 10 and 11 engage the inner portions of the limbs. The wedge shaped block A has a front face 12 which has Velcro strips 13 positioned at spaced points for fastening the strapping B. The strapping B is constructed of elongated relatively wide strips which are provided with complimentary Velcro fastening means 14 at inner end portions thereof so as to enable the strap ends to be fastened thereto with the body portion of the straps passing about the limbs of the patient and the back of the abduction pillow as illustrated in FIGS. 1 and 4.

Figure 2:
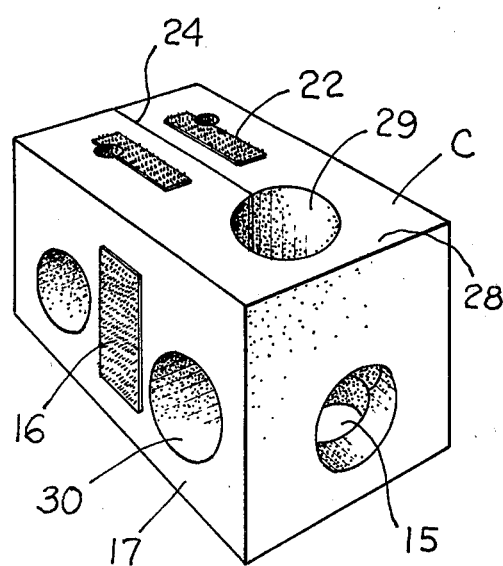
FIG. 2 is a perspective view illustrating a foam block foot and ankle support portion constructed in accordance with a modified form of the present invention.
Figure 3:
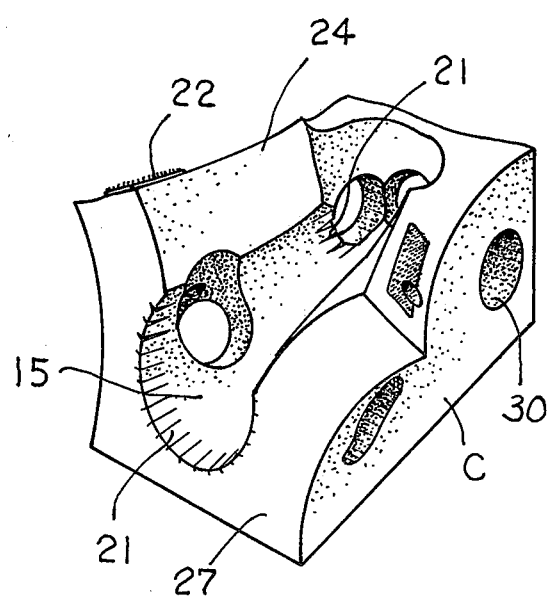
FIG. 3 is a perspective view further illustrating the slotted portions of the foam support block.

The block portions C are best illustrated in FIGS. 2 and 3, and it will be observed that an elongated longitudinal opening or bore 15 is provided therein for accommodating the leg and ankle portion of the wearer. A Velcro hook tape strip 16 is provided on a side 17 thereof for reception upon a complementary Velcro loop tape strip 18 carried adjacent the remote corners of the wedge shaped body A. A slot 19 is cut out of the block, shown in FIG. 1, or a recess 20 may be provided in the wedge shaped body A as illustrated in FIG. 4 for attaching the blocks C by means of the complementary Velcro strips adjacent the remote corners of the wedge shaped body for supporting the foot and ankle portions of the patient.

The longitudinal slots 21 are illustrated in FIG. 3 as being formed at both ends of the elongated longitudinal opening for relieving the pressure against the limb of the user in these areas so as to offer support but minimize the pressure exerted in these critical areas. Velcro strips 22 are provided adjacent an upper surface of the block for receiving straps 23 for closing the slot 24 which is provided for receiving the foot and ankle portions within the elongated block.

Figure 5:
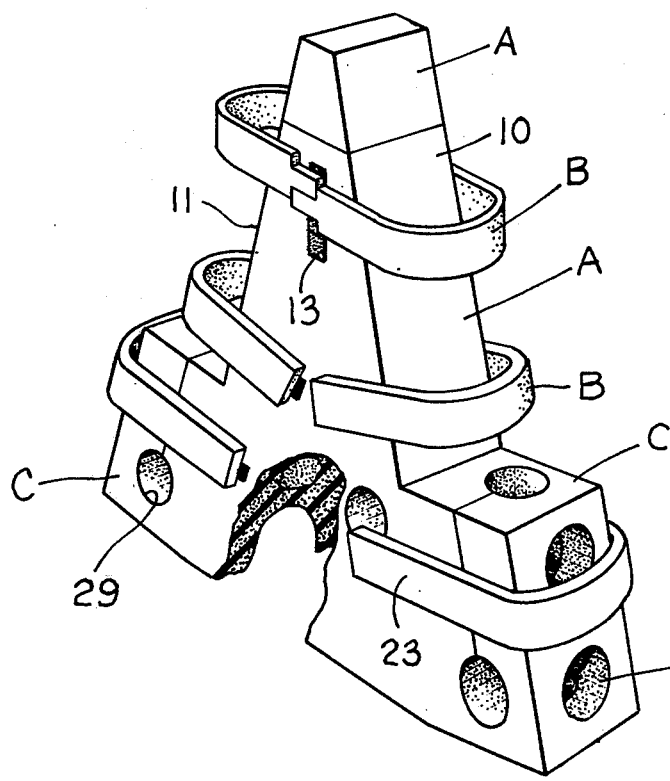
FIG. 5 is a perspective view further illustrating the invention in a further modified form.

FIG. 5 illustrates a somewhat further modified form of the invention in which the block portions C are integral with the wedge shaped body. In each instance, additional openings such as 26 may be provided for offering a honeycomb effect for further ventilation to the extremeties. While there is a tendency for foam material, especially polyurethane which is preferable, to allow air circulation, such may be facilitated by the openings 26 which are illustrated at desirable points through the construction of the abduction pillow.

It will be noted that the bore 15 is positioned in an intermediate portion of the block to provide a lower cushion 27 for the foot and ankle portions supporting same above the bed. A transverse support 28 is defined between the bore and the other end of the block and a vertical opening 29 extends from the top of the block to the bore for accommodating the foot and toe portion of the patient. The longitudinal opening or slit 24 extends from the vertical opening to one end of the block for receiving the foot and ankle portion for reception with interior surfaces of the bore. Thus, the transverse support prevents foot drop and interior surfaces of the bore prevent rotation of the limb while yieldably supporting same. A transverse bore 30 intersects the longitudinal bore adjacent the transverse support extending into the lower cushion providing a depression to accommodate the heal of the foot and to provide ventilation.

It is thus seen that an orthopedic support has been provided which permits the patient to be turned in the bed or positioned on the side while the limbs are supported and fixed against rotation. A continuous support is provided for the full length of the limb and the support may be readily personalized to suit individual patients. The device is inexpensive and designed for one patient use for the duration of treatment, although it may be readily autoclaved. The limbs are supported at all times in a manner to prevent foot drop and for the prevention of the cutting off of circulation as might result in the formation of decubitus ulcers. The time of nurses and other hospital personnel is reduced for the user of a device constructed in accordance with the present invention because such patient may be left unattended for greater periods of time.

While a preferred embodiment of the invention has been described using specific terms, such description is for illustrative purposes only, and it is to be understood that changes and variations may be made without departing from the spirit or scope of the following claims.

What is claimed is:

1. An abduction pillow for immobilizing the lower limbs of orthopedic patients comprising:
    a flat wedge shaped body constructed of uncovered synthetic foam material tapering outwardly at opposite sides;
    spaced strapping constructed of flat strips of synthetic foam material extending about spaced portions of each limb fixing same against respective sides of said body maintaining said limbs in divergent fixed positions corresponding to the divergent disposition of said sides; and
    a block constructed of synthetic foam material having an internal cavity therein carried adjacent a lower corner of said wedge shaped body for receiving and supporting the foot and ankle portions of said limbs.

2. An abduction pillow for immobilizing the lower limbs of orthopedic patients comprising:
    a flat wedge shaped body constructed of uncovered synthetic foam material tapering outwardly at opposite sides;
    said wedge shaped body being of substantially uniform thickness;
    spaced strapping constructed of flat substantially rectangular strips of synthetic foam material extending about spaced portions of each limb fixing same against respective sides of said wedge shaped body, said wedge shaped body between said sides maintaining said limbs in divergent fixed positions corresponding to the divergent disposition of said sides; and
    spaced Velcro fastening tape means carried at spaced positions on said wedge shaped body and on one side adjacent the ends of said strapping;
    whereby said strapping may be fastened about said limbs at spaced locations therealong for immobilizing the limbs in spread position.

3. An abduction pillow for immobilizing the lower limbs of orthopedic patients comprising:
    a flat wedge shaped body constructed of uncovered synthetic foam material tapering outwardly at opposite sides;
    said wedge shaped body being of substantially uniform thickness;
    spaced strapping constructed of flat substantially rectangular strips of synthetic foam material extending about spaced portions of each limb fixing same against respective sides of said wedge shaped body maintaining said limbs in divergent fixed positions corresponding to the divergent disposition of said sides;
    spaced Velcro fastening tape means carried at spaced positions on said wedge shaped body and on one side adjacent the ends of said strapping;
    an elongated substantially rectangular block of synthetic foam material carried adjacent a lower corner of each lower corner of said wedge shaped body; a longitudinal bore opening at one end of said rectangular block and terminating short of the other end of said rectangular block;

said bore being positioned in an intermediate portion of said block to provide a cushion for the foot and ankle portions supporting same above the bed;

a transverse support defined between said bore and said other end of said block and a vertical opening extending from the top of the block to said bore for accommodating the foot and toe portion of the patient; and a longitudinal opening extending from said vertical opening to said one end of said block for receiving the foot and ankle portion for reception within interior surfaces of said bore;

whereby said strapping may be fastened about said limbs at spaced locations therealong for immobilizing the limbs in spread position and preventing foot drop and ankle rotation.

4. The structure set forth in claim 3 including means for removably positioning said blocks adjacent lower corners of said wedge shaped body.

5. An orthopedic support for cradling the ankle and foot portions of the lower extremeties of an orthopedic patient during bedrest comprising:

an elongated substantially rectangular block of synthetic foam material;

a longitudinal bore opening at one end of said rectangular block and terminating short of the other end of said rectangular block;

said bore being positioned in an intermediate portion of said block to provide a lower cushion for the foot and ankle portions supporting same above the bed;

a transverse fixed support defined between said bore and said other end of said block and a vertical opening extending from the top of the block to said bore for accommodating the foot and toe portion of the patient; and a longitudinal opening extending from said vertical opening on an upper side of said block for receiving the foot and ankle portion for reception within interior surfaces of said bore;

whereby said transverse support prevents foot drop and interior surfaces of said bore preventing rotation of the limb while yieldably supporting same.

6. The structure set forth in claim 5 including a plurality of circumferentially spaced longitudinal slits in said lower cushion adjacent said opening at one end of the block and adjacent said transverse bore.

* * * * *